(12) United States Patent
Meyer

(10) Patent No.: US 9,060,804 B2
(45) Date of Patent: *Jun. 23, 2015

(54) APPARATUS AND METHOD FOR CLEANING MICROSURGICAL INSTRUMENTS

(75) Inventor: Rolf Meyer, Biel-Bienne (CH)

(73) Assignee: ASICO, LLC., Westmont, IL (US)

(*) Notice: Subject to any disclaimer, the term of this patent is extended or adjusted under 35 U.S.C. 154(b) by 0 days.

This patent is subject to a terminal disclaimer.

(21) Appl. No.: 11/864,865

(22) Filed: Sep. 28, 2007

(65) Prior Publication Data
US 2014/0352724 A1    Dec. 4, 2014

(51) Int. Cl.
*B08B 3/04* (2006.01)
*A61B 19/00* (2006.01)
*A61F 2/16* (2006.01)

(52) U.S. Cl.
CPC ......... *A61B 19/34* (2013.01); *A61F 2250/0092* (2013.01); *A61F 2/1662* (2013.01)

(58) Field of Classification Search
CPC ...................................................... A61B 19/34
See application file for complete search history.

(56) References Cited

U.S. PATENT DOCUMENTS

| | | | | |
|---|---|---|---|---|
| 5,400,767 | A * | 3/1995 | Murdoch | 600/157 |
| 5,755,894 | A * | 5/1998 | Bowman et al. | 134/22.12 |
| 8,741,069 | B2 * | 6/2014 | Meyer | 134/22.1 |

* cited by examiner

*Primary Examiner* — Michael Barr
*Assistant Examiner* — Jason Riggleman
(74) *Attorney, Agent, or Firm* — Wood, Phillips, Katz, Clark & Mortimer

(57) ABSTRACT

A cleaning apparatus for microsurgical instruments of the type having screw-type mechanisms used to advance or retract a plunger has a hollow sleeve into which the injector is liquid-tightly inserted, the sleeve being configured to hold the plunger in a fixed position when the plunger is disengaged from the injector body. A cap having an inlet port is liquid-tightly attached to the sleeve and cleaning liquid is forced from a syringe into and through the inlet port, flushing detritus from the injector. Various sizes and shapes of sleeves are used to accommodate different injectors.

7 Claims, 4 Drawing Sheets

APPARATUS AND METHOD FOR CLEANING MICROSURGICAL INSTRUMENTS

FIELD OF THE INVENTION

The present invention relates generally to microsurgical instruments and, more particularly, to methods and apparatus for cleaning such instruments prior to sterilization.

BACKGROUND OF THE INVENTION

Sterilization of surgical instruments and apparatus is an absolutely essential step in the performance of successful surgeries. Where surgical instruments such as knives, scalpels and the like are used, sterilization is facilitated by the fact that such instruments have no moving parts, leaving all operative surfaces exposed to sterilizing solutions and sterilizing steam or other heated gases.

Ophthlamological surgical techniques involve the use of extremely small instruments commonly referred to as "microsurgical instruments." Many of these instruments not only have moving parts, but have parts that are placed within tubes or other channels. One example of such an instrument is known as a cartridge injector, an instrument used to accept a cartridge within which an intraocular lens (IOL) is folded and placed. A plunger in the injector is then moved through a channel to extend a plunger tip which contacts the lens and forces it through an opening at the end of a cartridge and into an incision formed in the eye.

Another commonly used microsurgical instrument is a microforceps. In this instrument, a pair of opposed surgical steel "strips" extend from a hollow tube. The tube, in turn, is attached to a carriage within the instrument and a handle linkage and mechanism which, when operated moves the carriage and, thereby, the tube forward to contact the two surgical steel strips to force them together. When the handle mechanism is relaxed, the tube is allowed to move rearwardly and the strips then separate.

Instruments such as the cartridge injector and microforceps are expensive and are not easily manufactured to be disposable which means that each must be cleaned and sterilized between uses. Because of their sizes and precise construction they are not easily disassembled to facilitate sterilization.

Both instruments are commonly used with a surgical procedure known as phacoemulsification in which an incision is made in the eye to remove a damaged or diseased lens by cutting the lens into pieces and then emulsifying and aspirating the lens particles. Thereafter, a foldable plastic IOL is folded, placed into a cartridge, inserted into a cartridge injector which is then operated to force the lens from the cartridge through the incision into the eye as a replacement for the damaged lens than has already been removed.

The microforceps is used to break the damaged or diseased lens into pieces prior to phacoemulsification. As can be appreciated, these instruments are extremely small in size, particularly given the fact that the incision made in the eye is preferably as small as possible to prevent leakage of eye fluid from the wound after surgery. Where such incisions are sufficiently small, they need not be sutured and will heal without appreciable leakage.

The problem of satisfactorily sterilizing and cleaning microsurgical instruments used in phacoemulsification has been addressed in an article entitled "Residual Debris as a Potential Cause of Post-Phacoemulsification Endophthalmitis," appearing in Eye (Basingstroke), Volume 17, No. 4, published May 2003 and written by T. Leslie, D. A. Aitken, T. Barrie, and C. M. Kirkness. The authors conducted a study of phacoemulsification instruments that had been sterilized to determine whether debris had been left behind after typical sterilization operations. Samples were taken from phacoemulsification instruments and from irrigation and aspiration instruments. Two studies were done, each at a different institution.

In the first study, 62 percent of the instruments were found to be clean, 16 percent were found to be moderately contaminated and 22 percent were severely contaminated. The second study produced similar results.

A third study compared instruments that had been cleaned by an automated flushing system prior to sterilization. Although not completely eliminating contamination, the technique of flushing prior to sterilization decreased the incidence of contaminated instruments. The flushing apparatus used was automatic in operation.

The prior art includes examples of attempts to provide means for flushing surgical apparatus prior to sterilization.

U.S. Pat. No. 5,225,001 (Manni) teaches and describes a single channel scope cleaning method and apparatus used to pump sterilizing solution through instruments used for endoscopy and arthroscopy. The cleaning apparatus is placed concentrically about the exterior surface of the probe and sterilizing solution is pumped through the cleaning apparatus and through the channel formed between the cleaner and the endoscopic apparatus.

U.S. Pat. No. 5,279,317 (Bowman) teaches and describes an endoscopic cannulated instrument flushing apparatus for forcing a flushing liquid through an endoscopic cannulated instrument for removal of gross debris. The instrument described in Bowman et al has a handle at one end and a surgical tool, such as a pair of gripping arms, at the other. The handle end remains outside the body while the tool end is inserted through an incision and comes into contact with tissue.

The apparatus has a flushing chamber into which the tool end of the instrument is inserted in a friction fit. Sterilizing flushing fluid is forced into the chamber and through the tool end of the endoscopic instrument to exit out of the handle end. The flow of the flushing liquid is thus from the tool end to the handle end, pushing any debris along the entire length of the instrument, requiring a passage large enough to allow such debris to travel all the way to the handle.

U.S. Pat. No. 5,511,568 (Bowman et al) teaches and describes an endoscopic cannulated instrument flushing apparatus for forcing a flushing liquid through an endoscopic cannulated instrument for removal of gross debris. This patent is a continuation-in-part of the earlier mentioned Bowman et al patent and adds a pressurized source of flushing liquid rather than a hand-operated syringe. As with its parent, the cleaning is done in a direction away from the tool end of the instrument.

None of these references are concerned with microsurgical instruments.

In co-pending application Ser. No. 11/534,573 cleaning apparatus and methods are described for use with a variety of microsurgical instruments, including those with plungers. The flushing and cleaning of an injector using a screw-type mechanism to advance the plunger is described in conjunction with flush channels formed at the closed end of the injector. The present invention addresses the task of flushing a screw-type injector without such flush channels.

Cartridge injectors have narrow and elongated housings through which a plunger is reciprocated to enter an IOL-holding cartridge and force the IOL out of the cartridge and through an incision into the eye.

Microforceps of the type described herein have pair of surgical steel strips which are placed in face-to-face relationship and along a portion of which a tubular housing is moved or reciprocated during surgery. It is this movement along the protruding surgical strips that may trap debris.

In both cases, the clearance between the outer tubular housing and the plunger or surgical strips is small and any debris trapped therewithin is not only a source for potential infection during a subsequent surgical procedure, but also a source of friction during surgery between moving parts of the respective instruments. This friction changes the "feel" of the instrument to the surgeon because of the extremely small operating field can have a serious effect on the surgery.

The microforceps and cartridge injectors described above are representative of microsurgical instruments which may differ in construction from those described herein but which exhibit the same problems when it comes to cleaning the instruments to remove surgical debris prior to sterilization.

SUMMARY OF THE INVENTION

It is an object of the present apparatus to provide a simply and economically constructed flushing apparatus allowing for the hand-flushing of microsurgical instruments.

It is another object of the present apparatus to provide such apparatus in which the flow of the flushing liquid is toward the operative or distal portion of the instrument rather than toward the proximal or handle portion.

Yet another object of the present apparatus is to provide a flushing mechanism which will protect the distal ends of the instrument so that they will not be damaged during flushing.

Yet another object of the present apparatus to construct such cleaning apparatus in such a manner in which the actual exit of the flushing liquid can be observed.

While the following describes a preferred embodiment or embodiments of the present apparatus, it is to be understood that this description is made by way of example only and is not intended to limit the scope of the present apparatus. It is expected that alterations and further modifications, as well as other and further applications of the principles of the present apparatus will occur to others skilled in the art to which the apparatus relates and, while differing from the foregoing, remain within the spirit and scope of the apparatus as herein described and claimed. Where means-plus-function clauses are used in the claims such language is intended to cover the structures described herein as performing the recited functions and not only structural equivalents but equivalent structures as well. For the purposes of the present disclosure, two structures that perform the same function within an environment described above may be equivalent structures.

These and further objects and advantages of the present apparatus will be best understood by reference to the accompanying drawings which illustrate use of the apparatus in the best mode presently known.

BRIEF DESCRIPTION OF THE DRAWINGS

The accompanying drawing figures illustrate the apparatus described herein in varying detail and describe details of various embodiments thereof. Drawing figures are exemplary only and are not drawn to scale.

DETAILED DESCRIPTION OF THE INVENTION

Figure 1:
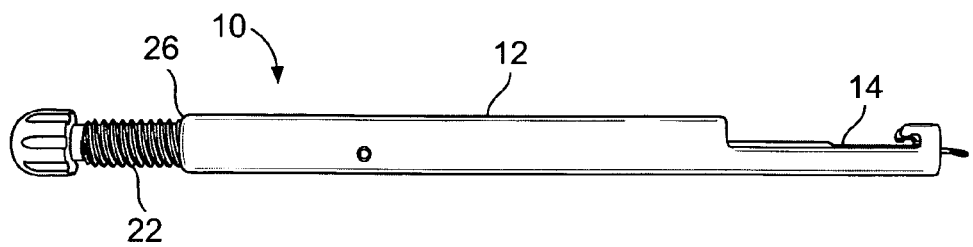
FIG. 1 is a lateral perspective view of a prior art cartridge injector with a screw-type mechanism for moving the injector plunger, showing the plunger in a substantially withdrawn position.

Referring now to FIG. 1 the numeral 10 indicates generally an injector for introducing an artificial intraocular lens (IOL) into a patient's eye. The injector shown herein is the Monarch® II IOL Delivery System manufactured by Alcon Laboratories, Inc. of Fort Worth, Tex. Injector 10 has a generally right-circular cylindrical body 12 having a cutout 14 formed at one end thereof adapted to grip a cartridge containing a folded IOL (not herein shown).

Figure 2:
FIG. 2 is the injector of FIG. 1 showing the plunger fully extended.
Figure 3:
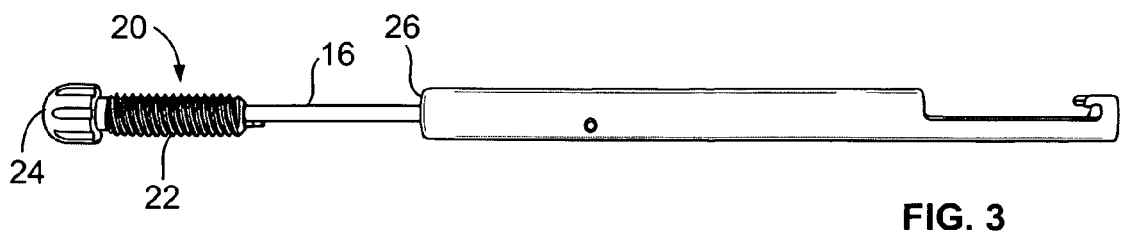
FIG. 3 is the injector of FIG. 1 showing the knob and screw disconnected from the injector body.

Injector 10 also has a plunger shaft 16 as partially shown in FIG. 3, at one end of which, as seen in FIG. 2, a pusher 18 is formed. Mounted to the other end of plunger shaft 16 is a screw knob 20 consisting of a threaded shaft 22 attached to a knob 24.

Screw knob 20 is rotatably attached to plunger shaft 16 such that when screw knob 20 is rotated, shaft 16 does not. Body 12 is internally threaded beginning at body end 26 and, as seen in FIG. 1, body 12 rotatably accepts threaded shaft 22 and plunger shaft 16 is advanced from and retracted into body 12 as knob 24 is rotated in a clockwise or counterclockwise direction. Restraining means (not shown) formed within body 12 prevents plunger shaft 16 from rotating as it is extended or retracted.

FIG. 1 shows the position of screw knob 20 when pusher 18 is almost completely retracted into body 12. 2 shows pusher 18 extended to its maximum from body 12 when knob 24 is turned to advance knob shaft 22 fully into body 12. FIG. 3 shows screw knob 20 disassembled from body 12. Restraining means (not shown) prevents knob shaft 20 and plunger 16 from being withdrawn from body 12.

Figure 4:
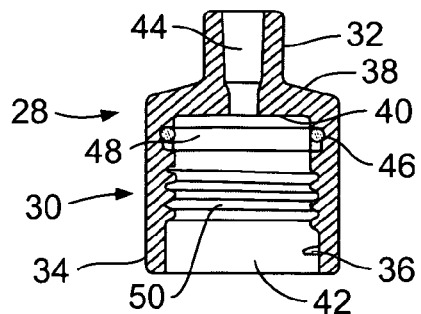
FIG. 4 is a lateral sectional view of the cap of an instrument cleaner embodying aspects of the present invention.

Referring now to FIG. 4, the numeral 28 identifies a sectional view of a cap, preferably formed from a high density thermoplastic material, used as a part of the instant invention. Cap 28 has a hollow, generally right-cylindrical cap body 30 terminating in an inlet port 32. Cap 30 has an outer wall 34, an inner wall 36, an upper outer wall 38 and an inner upper wall 40 defining a cap cavity 42. Inlet port 32 has a central inlet passage 44 communicating with cavity 42 to form a liquid flow path as described later.

An inner annular groove 46 forms a seat for an O-ring 48, and a series of ridges or screw threads 50 are formed on interior wall 36.

Figure 5:
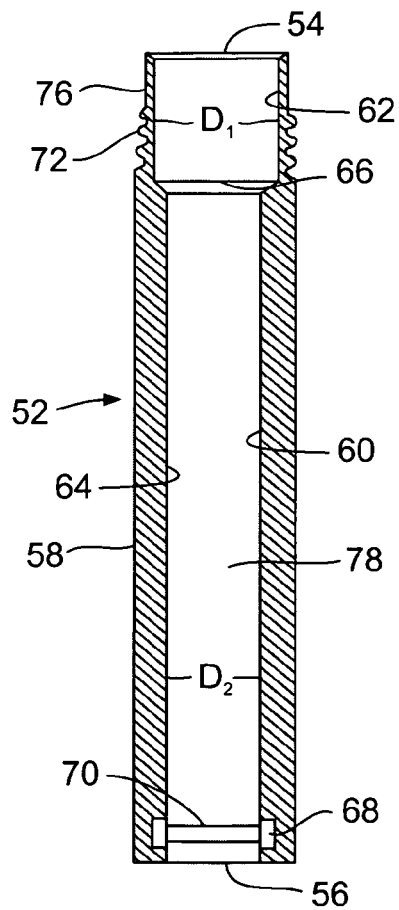
FIG. 5 is a lateral sectional view of the sleeve of an instrument cleaner adapted to mate with the cap of FIG. 4.

Referring now to FIG. 5 the numeral 52 identifies a sectional view of a cleaning sleeve. preferably formed from high-density thermoplastic material. Sleeve 52 is hollow and is generally formed as a right cylindrical tube of varying cross-sectional dimensions, sleeve 52 having an inlet end 54 and an outlet end 56. Sleeve 52 has an outer wall 58 and an inner wall 60.

Sleeve 52 has a first inner segment 62 with and inner diameter $D_1$ beginning at inlet end 54 and a second inner segment 64 with an inner diameter $D_2$ beginning at outlet end 56 with $D_1$ being larger than $D_2$. Segments 62 and 64 meet at and define an inner shoulder 66. An inner annular groove 68 is formed proximate outlet end 56 and forms a seat for an O-ring 70. A series of ridges or screw threads 72 are formed on outer wall 58 proximate inlet end 54.

Figure 6:
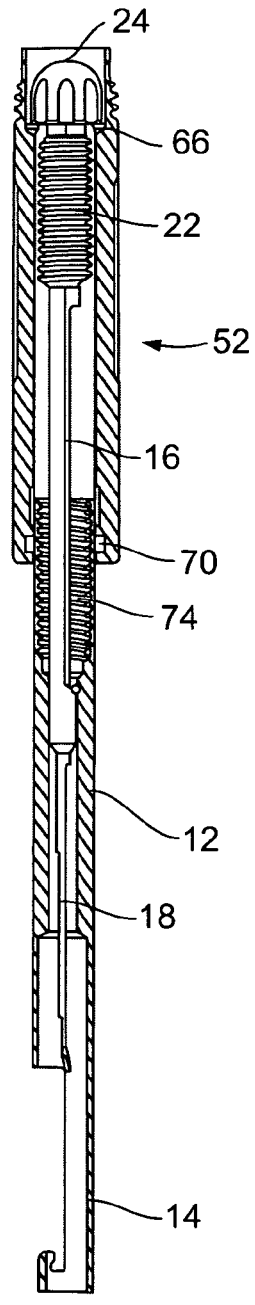
FIG. 6 is a schematic sectional view of the sleeve of FIG. 5 positioned on the injector of FIG. 3.

Referring now to FIG. 6 the use of one form of the present invention can be explained. Screw knob 20 is unthreaded from body 12 of injector, disengaging threaded shaft 22 from internal injector threads 74 10 as shown in FIG. 3. Injector 10 is then inserted into sleeve 52 by inserting that portion of body 12 having cutout 14 into sleeve inlet 54. Sleeve 54 is then moved along injector body 12 until shoulder 66 contacts knob 24, thus holding plunger 16 in a disengaged position with respect to plunger body 12. In this position pusher 18 is held within and is protected by injector body 12. Preferably, inner diameter $D_2$ is selected and groove 68 is positioned such that O-ring 70 contacts body 12 in a liquid-tight friction fit when shoulder 66 is in contact with knob 24.

Figure 7:
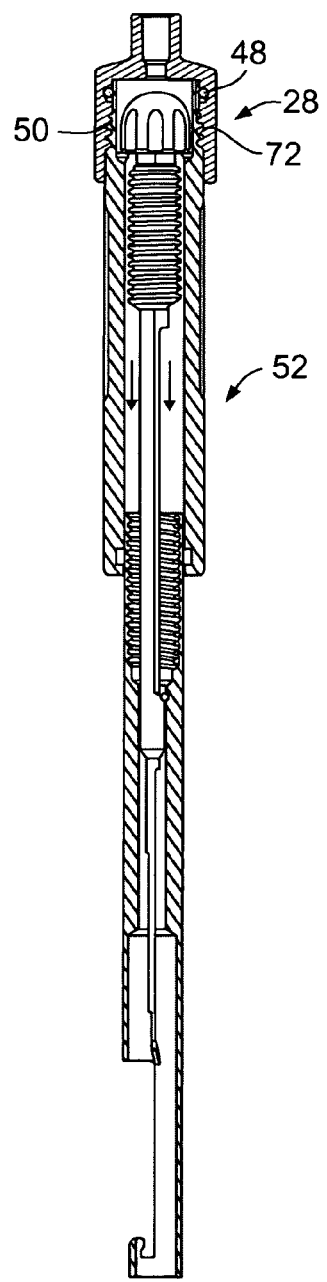
FIG. 7 is a schematic sectional view of the cap of FIG. 4 attached to the sleeve as shown in FIG. 6.
Figure 8:
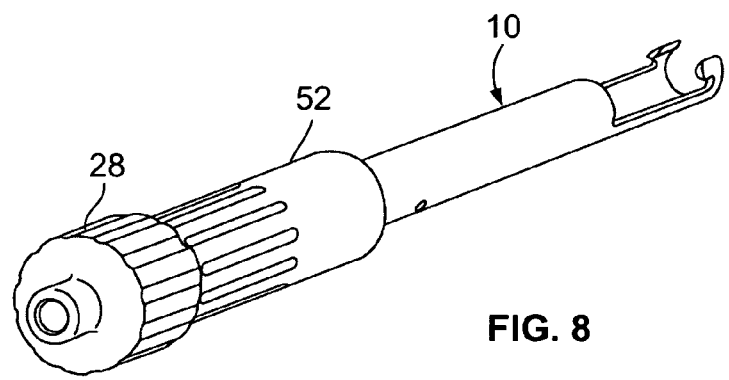
FIG. 8 is a perspective view of the cap and sleeve positioned on the injector of FIG. 3.

Referring now to FIG. 7, cap 28 is shown attached to sleeve 52, with cap ridges or threads 50 interengaging with sleeve ridges or threads 72. Preferably, groove 46 is positioned to allow O-ring 48 to form a liquid-tight seal with outer wall 76 of sleeve inlet end 54 while the interior wall segment 60 of sleeve 52 forms a flush chamber 78. FIG. 8 shows cap 28 interengaged with sleeve 52 as positioned on injector 10.

Figure 9:
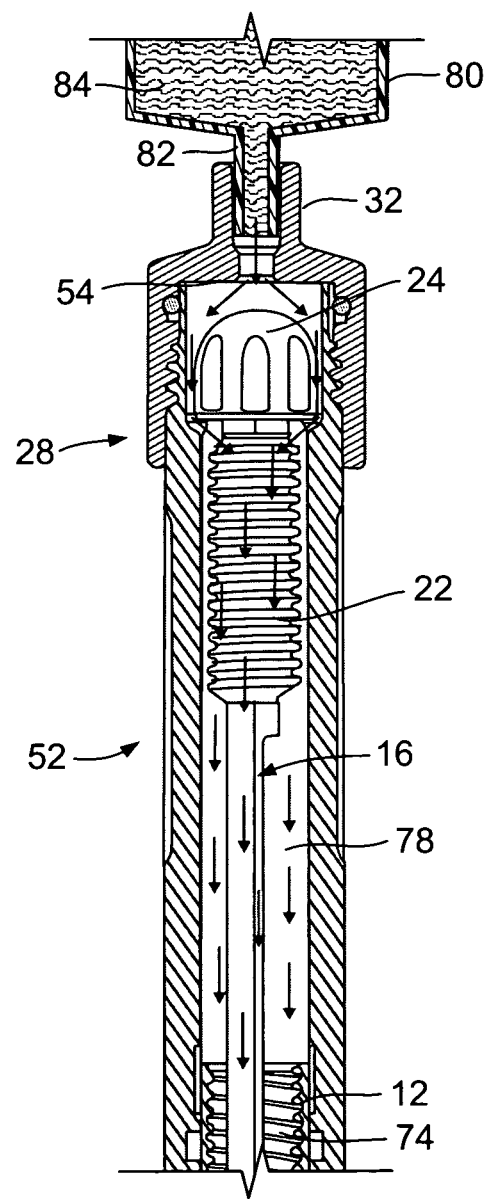
FIG. 9 is a partial schematic sectional view of FIG. 7 showing the flow path of cleaning liquid.

Referring now to FIG. 9 a partial sectional view of FIG. 7 is shown with a syringe 80 positioned to insert the syringe spout 82 into inlet port 32 of cap 28. Syringe 80 is filled with a cleaning and flushing liquid 84 which is then forced under pressure through spout 82 and inlet port 32 to the interior of sleeve 52, around knob 24 and threaded shaft 22 and around plunger shaft 16 and into body 12, contacting threads 74 and exiting at cutout 14, thereby flushing detritus from injector 10. Afterwards, cap 28 and sleeve 52 are removed from injector 10 which is then sterilized and readied for further use.

It is recognized that other screw-type injectors will have geometries and dimensions differing from the injector used as an example herein and it is a feature of the present invention to furnish cleaners comprising caps and sleeves made to accommodate such variations while still employing the principles and allowing the practice of the invention as described and claimed herein.

What is claimed is:

1. A combination of an apparatus for cleaning a surgical instrument and a surgical instrument, said combination comprising:

said surgical instrument, said surgical instrument having a hollow body having an internal passageway, said passageway having an inlet and an outlet, said inlet threadably receiving a plunger mechanism, said plunger mechanism having a knob positioned outside said body, said apparatus, said apparatus having a hollow flush chamber having first and second ends, said second end configured to receive said hollow instrument body, outlet end first, said first end engaging said instrument body in a liquid tight manner;

said second end configured to engage said knob when said plunger mechanism is unthreaded from said inlet thereby positioning said knob and at least a portion of said plunger mechanism within said flush chamber;

a flush plug liquid-tightly closing off said second end of said flush chamber over said knob, said flush plug having an inlet port communicating with said flush chamber, whereby liquid injected through said inlet port passes through said flush chamber, enters said passageway inlet, passes through said passageway and exits through said passageway outlet, whereby debris in said instrument is flushed in a direction away from said knob.

2. The combination as recited in claim 1 wherein said liquid is injected through said inlet port by a hand-held syringe.

3. The combination as recited in claim 1 wherein said flush chamber is a cylinder having a circular cross-sectional configuration.

4. The combination as recited in claim 1 wherein said flush plug is threadably attached to said flush chamber.

5. The combination as recited in claim 1 wherein said flush plug is attached to said flush chamber with a friction fit.

6. The combination as recited in claim 1 wherein said instrument is of the type wherein said instrument plunger, when unthreaded from said inlet end extends a maximum distance from said instrument without disengaging from said instrument and said flush chamber is configured to engage said knob with said second end and hold said plunger at said maximum distance.

7. The combination as recited in claim 1 further comprising a reservoir for said liquid, said reservoir attachable to said inlet port; and said reservoir capable of forcing said liquid into said inlet port.

\* \* \* \* \*